United States Patent
Newmark et al.

(10) Patent No.: US 6,242,012 B1
(45) Date of Patent: Jun. 5, 2001

(54) HERBAL COMPOSITION FOR PROMOTING HORMONAL BALANCE IN WOMEN AND METHODS OF USING SAME

(76) Inventors: Thomas Newmark, 704 Cordell Ct., St. Louis, MO (US) 63132; Paul Schulick, 222 Kipling Rd., Brattleboro, VT (US) 05301

( * ) Notice: Subject to any disclaimer, the term of this patent is extended or adjusted under 35 U.S.C. 154(b) by 0 days.

(21) Appl. No.: 09/512,674

(22) Filed: Feb. 25, 2000

Related U.S. Application Data

(60) Provisional application No. 60/160,216, filed on Oct. 19, 1999.

(51) Int. Cl.[7] ............................ A61K 35/78; A01N 65/00
(52) U.S. Cl. ........................ 424/756; 424/451; 424/452; 424/455; 424/464; 424/465; 424/489; 424/773; 424/777; 514/23; 514/27; 514/627; 514/825; 514/827; 514/886
(58) Field of Search .................................. 424/195.1, 451, 424/452, 455, 464, 465, 489, 756, 773, 777; 514/627, 886, 825, 827, 23, 27, 916

(56) References Cited

U.S. PATENT DOCUMENTS

| | | |
|---|---|---|
| 5,017,397 * | 5/1991 | Nguyen et al. ................... 426/542 |
| 5,120,558 | 6/1992 | Nguyen et al. . |
| 5,565,199 | 10/1996 | Page et al. . |
| 5,569,459 | 10/1996 | Shlyankevich . |
| 5,707,630 | 1/1998 | Morrow . |
| 5,874,084 | 2/1999 | Yng-Wong . |
| 5,891,440 | 4/1999 | Lansky . |
| 5,908,628 | 6/1999 | Hou . |
| 5,932,101 | 8/1999 | Kanel et al. . |

* cited by examiner

Primary Examiner—Herbert J. Lilling
(74) Attorney, Agent, or Firm—Patton Boggs LLP

(57) ABSTRACT

An herbal composition which can be used to alleviate the symptoms associated with hormonal imbalance in women contains supercritical extracts of ginger, rosemary and evening primrose oil, and either regular or supercritical (preferably regular) extracts of black cohosh, dong quai, schizandra berry, chaste tree berry and rosemary. The herbal composition can be administered orally, topically or parenterally. In addition to promoting hormonal balance, the herbal composition also promotes normal bone growth by inhibiting the 5-lipoxygenase enzyme and sustains warmth and normal fluids for healthy sexual functioning. Furthermore, the herbal composition contains organic anti-aging constituents that inactivate free radicals, thereby providing antioxidant activity.

6 Claims, No Drawings

HERBAL COMPOSITION FOR PROMOTING HORMONAL BALANCE IN WOMEN AND METHODS OF USING SAME

This application claims benefit under 35 USC 119(e) of provisional 60/160,216 filed Oct. 19, 1999.

BACKGROUND OF THE INVENTION

This invention relates to herbal compositions. More particularly, this invention relates to an herbal composition which can promote pre- and postmenopausal hormonal balance in women. The present invention further relates to methods of using such composition to promote hormonal balance.

From the commencement of menstruation until the termination of menopause, the female body can experience wide fluctuations in baseline hormonal levels. When such fluctuations cause an imbalance in the hormonal composition, certain chemical reactions occur which cause what are commonly referred to as PMS and/or menopausal symptoms. These symptoms include headaches, cramping, nausea, inflammation, increased agitation, anxiety, tension, restlessness, decreased digestive tract activity, depression, moodiness and severe mood swings.

Hormone Replacement Therapy (RWI) and conventional treatments for hormonal imbalance conditions like PMS in women are the subject of countless articles and controversy. Few would question that the treatment protocols are fraught with acute side effects and potential long term health concerns. A search for historically safe and effective hormonal health/balance programs with a basis in modern science is of great need for women today.

According to a growing body of research, the eicosanoid cascade plays a critical role in women's health and hormonal balance. An imbalance correlates not only with uncomfortable menstrual cycles, resulting in conditions like PMS, but also might relate to serious degenerative conditions like osteoporosis, heart disease and cancer. Historical and scientific research confirms that herbal alternatives exist which can safely bring more comfort and balance to a women's hormonal cycles.

Herbs which are known to be useful in alleviating symptoms associated with hormonal balance in women include, e.g., schizandra, ginger, black cohosh, and vitex extract.

Compounds in schizandra called schizandrins have been found to have comparable or stronger free radical scavenging capability than vitamins C and E. Reference is made, e.g., to *Cell Biol Int Rep* February 1990;14(2):99–109 Scavenging effect of schizandrins on activeoxygen radicals. Zhao B L, Li X J, Liu G T, Jia W J, Xin W J Institute of Biophysics, Academia Sinica, Beijing, China.; and *Free Radic Biol Med* 1990;9(2):99–104 Scavenging effects on active oxygen radicals by schizandrins with different structures and configurations. Li X J, Zhao B L, Liu G T, Xin W J Institute of Biophysics, Academic Sinica, Beijing, China. Relief of oxidative stress is important in a number of health conditions associated with hormonal health.

Ginger contains at least one constituent which is active against 5-lipoxygenase. Reference is made, e.g., to *Chem Pharm Bull* (Tokyo) February 1992;40(2):387–91 Inhibition of prostaglandin and leukotriene biosynthesis by ginerols and diarylheptanoids. Kiuchi F, Iwakami S, Shibuya M, Hanaoka F, Sankawa U Faculty of Pharmaceutical Sciences, University of Tokyo, Japan; *Prostaglandins Leukot Med* October 1986;24(2–3);195–8 Inhibition of human neutrophil 5-lipoxygenase activity by gingerdione, shogaol, capsaicin and related pungent compounds. Flynn D L, Rafferty M F, Boctor A M; *Nippon Yakurigaku Zasshi* October 1986;88(4):263–9 [Pharmacological studies on ginger. IV. Effect of (6)-shogaol on the arachidonic cascade]. Suekawa M, Yuasa K, Isono M, Sone, H, Ikeya Y, Sakakibara I, Aburada M, Hosoya E; *Cancer Res* February 1991;51(3):813–9 Inhibitory effects of curcumin on in vitro lipoxygenase and cyclooxygenase activities in mouse epidermis. Huang M T, Lysz T, Ferraro T, Abidi T F, Laskin J D, Conney A H Department of Chemical Biology and Pharmacognosy, College of Pharmacy, Rutgers, State University of New Jersey, Piscataway, N.J. 0885-0789; and *Prostaglandins Leukot Med* June 1986;22(3):357–60 Inhibition of 5-hydroxy-eicosatetraenoic acid (5-HETE) formation in intact human neutrophils by naturally-occurring diarylheptanoids: inhibitory activities of curcuminoids and yakuchinones. Flynn D L, Rafferty M F, Boctor A M. Thus, ginger has been found to exhibit anti-inflammatory properties.

Ginger also exhibits anti-oxidant benefits.

Black cohosh has been found to be a safe, effective alternative to estrogen replacement therapy for those patients in whom estrogen replacement therapt is either refused or contraindicated. Reference is made, e.g., to *Womens Health* June 1998;7(5):525–9 A review of the effectiveness of *Cimicifuga racemosa* (black cohosh) for the symptoms of menopause. Leiberman S University of Bridgport, Conn., USA.; and *Adv Ther* January–February 1998;15(1):45–53 Therapeutic efficacy and safety of *Cimifuga racemosa* for gynecological disorders. Liske E Schaper & Brummer GmbH & Co. KG, International Sales Division, Salzgitter-Ringelheim, Germany.

Vitex extract is effective n treatment of PMS luteal phase defects due to latent hyperprolactinaemia. See, e.g., *Arzneimittelforshung* July 1993;43(7):752–6 [Vitex agnus castus extract in the treatment of luteal phase defects due to latent hyperprolactinemia. Results of a randomized placebo-controlled double-blind study]. Milewicz A, Sworen H, Sienkiewicz K, Jedrzejak J, Teucher T, Schmitz H Abteilung fur Endokrinologie, Medizinizche Hocschule, Hamburg.

Other References which teach the use of herbs to relieve symptoms caused by female hormonal imbalances are, e.g., U.S. Pat. Nos. 5,569,459; 5,707,630; 5,891,440; 5,565,199; and 5,874,084.

Given the changing characteristics of the hormaonal imbalance during the menstrual cycle and/or menopause, as well as the variations in the specific hormonal imbalance from person to person, it would be advantageous to introduce a compound which adapts to meet the specific needs of each person, both over time and from person to person. Herbs have been found to meet such needs.

The human body is able to identify the chemical components in which it is deficient. An interesting and important feature of herbal interaction with the human body is the fact that the body will only absorb from an herbal compound those chemical components in which the body is deficient. Those chemical components of the herbal compound which are not needed simply pass through the body without undue stress placed on the body.

Thus, although it is known to use certain herbs to relieve symptoms associated with hormonal imbalance in women, the benefits associated with the use of herbs makes it continually desirable to provide alternative herbal compositions for providing such relief.

It is also continually desirable to provide a herbal composition which, in addition to relieving symptoms of hormonal imbalance, is also able to scavenge oxygen free radicals, thus providing antioxidant benefits.

Herbs which are known to possess antioxidant properties include, e.g., ginger and rosemary.

A further desirable characteristic of an herbal composition designed to promote hormonal balance is the ability to inhibit the enzyme 5-lipoxygenase. Recent scientific research has shown that estrogen may promote bone growth by inhibiting this enzyme. According to the USDA Phytochemical Database, ginger and rosemary extracts inhibit 5-lipoxygenase.

Accordingly, a primary object of this invention is to provide an herbal composition which is capable of relieving symptoms associated with pre- and postmenopausal hormonal imbalance.

A further object of this invention is to provide an herbal composition which, in addition to promoting hormonal balance in women, is also capable of providing antioxidant benefits.

Another object of this invention is to provide a hormonal balance promoting herbal composition which is capable of inhibiting the enzyme 5-lipoxygenase, thereby promoting normal bone growth and healthy sexual functioning.

Yet another object of this invention is to provide a hormone-balancing herbal composition which is capable of sustaining warmth and normal fluids for healthy sexual functioning.

A still further object of this invention is to provide an orally, topically or parenterally administered herbal composition which can relieve symptoms of hormonal imbalance in women.

Yet another object of this invention is to provide a method of relieving symptoms of hormonal imbalance in women, using an herbal composition having the characteristics set forth in the preceding objects.

These and other objects are achieved in the present invention.

SUMMARY OF THE INVENTION

The present invention provides a unique formulation which incorporates an herbal polyphytonutrient approach to hormonal balance. The formulation of this invention combines the following features:

lipoxygenase inhibiting constituent compounds (ginger, rosemary)

empirically revered normalizers of hormonal functioning (black cohosh, vitex)

Essential Fatty Acid Modulators (Evening Primrose oil, Olive Oil)

Systemic mood/energy support (Dong Quai, Schizandra).

More specifically, the herbal composition of this invention the herbal composition of the present invention contains therapeutically effective amounts of the supercritical extracts of ginger, rosemary and evening primrose oil, and therapeutically effective amounts of either regular or supercritical (preferably regular) extracts of black cohosh, dong quai, schizandra berry and chaste tree berry.

The herbal composition of this invention can be administered orally, topically or parenterally. Thus, the present invention further provides a composition composed of the herbal active-ingredient composition in combination with a pharmaceutically acceptable oral, topical or parenteral carrier. In preferred embodiments, the herbal composition is orally administered as a soft gel capsule or topically administered as a cream.

The present invention also provides methods of using the herbal composition of this invention to alleviate symptoms of hormonal imbalance in women.

In the present invention, extracts are selected (when possible) which highlight and insure the active compounds are present and in meaningful quantity. This is achieved by means of supercritical-solvent free extraction technology, which allows for the highest potency of active compounds, as much as 250× original fresh plant material improving compliance and efficacy. Such technology allows the herbal composition to be made without chemical solvents.

DETAILED DESCRIPTION OF THE INVENTION

As stated above, the present invention provides an herbal active-ingredient composition capable of promoting hormonal balance in women.

The active-ingredient composition contains extracts taken from ginger, black cohosh, rosemary, dong quai, schizandra berries, chaste tree berries and evening primrose oil. As used herein, the term "extract" is intended to mean a concentrate of water-soluble and/or alcohol-soluble plant components from the portion of the plant extracted and can be in aqueous or powdered form. In the present invention, the extracts from ginger, rosemary and evening primrose oil are obtained using a supercritical extraction process as discussed later herein. These extracts are referred to herein as "supercritical extracts". The extracts from black cohosh, dong quai, schizandra berries and chaste tree berries can be prepared using either a supercritical extraction process or a conventional extraction process. If prepared using a conventional extraction process, the extracts will be referred to herein as "regular extracts" as a means of distinguishing these extracts from the supercritical extracts. In preferred embodiments of the present invention, the extracts of black cohosh, dong quai, schizandra berries and chaste tree berries are regular extracts.

Black cohosh is a phytoestrogenic balancing tonic. In the present invention, the extract of the black cohosh herb is preferably taken from the root and rhizome of the plant.

Ginger, part of the zingiberaceae family, diminishes headaches, uterine pain from any cause at the menstrual epoch and other general aches and pains; stimulates peripheral circulation; aids in digestion; and has antimicrobial effects. Ginger also exhibits antioxidant properties, due to the presence therein of anti-aging constituents that inactivate free radicals. Ginger further contains constituents which, like the hormone estrogen, inhibit an enzyme called 5-lipoxygenase. Recent scientific research suggests that estrogen may promote bone growth by inhibiting 5-lipoxygenase. Thus, the ginger supercritical extract used in the present invention may play a role similar to that of estrogen in bone maintenance capability. The supercritical extract of ginger used in the present invention is preferably taken from the rhizome.

Rosemary is a rich source of anti-aging constituents which inactivate free radicals. Thus, rosemary provides antioxidant benefits. Rosemary further includes phytonutrients which optimize memory. Rosemary further contains constituents which, like estrogen, inhibit 5-lipoxygenase. Thus, like the ginger supercritical extract used in the present invention, the rosemary supercritical extract may play a role in supplementing natural estrogen's bone maintenance capability. The rosemary supercritical extract is preferably obtained from the leaves and essential oil of the plant.

Dong Quai (*Angelica sinensis*) promotes vitality and internal harmony. Preferably, the extract (regular or supercritical) of the Dong Quai herb is taken from the root.

Schizandra berries (*Schizandra chinensis*) aid detoxification and promote normal fluids for healthy sexual functioning.

The chaste tree berry extract aids in promoting hormonal balance.

Evening primrose oil also helps to maintain hormonal health.

As stated hereinabove, the active-ingredient composition of this invention contains the supercritical extracts of ginger, rosemary and evening primrose oil. Supercritical extraction of these herbs can be carried out according to known supercritical extraction methods. Such methods are disclosed, e.g., in U.S. Pat. Nos. 5,932,101 and 5,120,558, both of which are hereby incorporated by reference herein.

U.S. Pat. No. 5,932,101 discloses a supercritical extraction process wherein an extraction solvent and a fluid feed are supplied with a countercurrent flow to an extraction column. The extraction solvent contains a dense gas (e.g., carbon dioxide), and the fluid feed contains at least one solute (e.g., an herb) and a carrier fluid (e.g., water). The solute is selective to the extraction solvent with respect to the carrier fluid. The carrier fluid contains at least one component which is barely soluble in the extraction solvent and substantially immiscible with the extraction solvent so as to provide two phases. The fluid feed and the extraction solvent intimately contact one another in the column for a sufficient amount of time to extract the solute from the carrier fluid to the extraction solvent. The column operates in an enhanced solubility region having a pressure of between 450 and 1200 bar and a temperature of between 50° C. and 300° C. The column has a diameter greater than about 3.5 centimeters and a height to diameter ratio of greater than about 5. A raffinate containing the carrier fluid is removed from the column, as is an extract containing the extraction solvent and the solute. The combination of pressure and temperature is sufficient for the solubility of the solute in the extraction solvent to be at least 250% by weight greater than the solubility of the solute in the extraction solvent at the same operating temperature but at a 200 bar pressure. Additionally, the solute may be separated from the extraction solvent in a phase separation device such as a decanter, a coalescer, a cyclone and a second extraction column.

The supercritical extraction process disclosed in U.S. Pat. No. 5,120,558 involves grinding a spice or herb and then extracting the ground spice or herb with supercritical fluid carbon dioxide under a pressure of from about 400 bar to about 600 bar and at a temperature of from about 80° C. to about 120° C. At least one oleoresin fraction is precipitated from the loaded supercritical fluid under a pressure of from about 280 bar to about 380 bar and at a temperature of from about 80° C. to about 100° C. Additional oleoresins may be obtained by next adjusting the pressure of the supercritical fluid to from about 100 bar to about 200 bar within the same temperature range of 80° C. to 100° C., and finally by reducing the pressure to from about 30 bar to about 50 bar and the temperature to from about 0° C. to about 30° C.

The dong quai, schizandra berry and chaste tree berry extracts used in the present invention can be prepared using either conventional or supercritical extraction techniques. Suitable conventional extraction techniques are disclosed, e.g., in U.S. Pat. Nos. 5,891,440; 5,874,084; and 5,908,628; all of which are hereby incorporated by reference herein.

For example, the dong quai, schizandra berry and chaste tree berry extracts used in the herbal composition of this invention can be prepared by contacting the herb with an appropriate solvent to form the extract. To make the extract suitable for oral administration, the solvent used must be substantially non-toxic to the subject so that there is no untoward level of adverse side effects, such as toxicity, irritation, allergy or hypersensitivity responses. The level of any such side effects should be commensurate with acceptable risk/benefit ratios. Examples of such substantially non-toxic solvents include water and ethanol.

In one extraction method which can be used herein, the plant portion to be extracted is placed into an extractor, 70% ethanol is added, and the resultant mixture is heated under reflux. Ethanol is recovered and condensed under low temperature and decompression until the specific density reaches 1.38 (thermal assay). The extract is then collected by vacuum drying.

The herbal composition of this invention can be prepared, for example, by individually washing, drying and grinding the herbs into fine powder, and then extracting the ground herbs (via supercritical extraction in the case of ginger, rosemary and evening primrose oil; and via either supercritical extraction or conventional extraction for black cohosh, dong quai, schizandra berry and chaste tree berry). The resulting extracts are then mixed together in amounts that are physiologically acceptable to the patient. No special mixing means is required. The mixture of extracts can be encapsulated, tableted or formulated with a physiologically acceptable vehicle into unit dosages.

The herbal active ingredient composition of this invention contains therapeutically effective amounts of the herbal extracts discussed above. With respect to the herbal extracts, the term "therapeutically effective amount" means that amount of the extract which, in conjunction with the amounts of the other herbal extracts present in the composition, will promote the ability of the overall composition to help alleviate the symptoms associated with hormonal imbalance in women.

As stated previously herein, the herbal composition of this invention can be administered in a variety of ways, including orally, topically (including ophtamically, vaginally, rectally, intranasally, and the like), and parenterally (e.g., by intravenous drip or by intraperitoneal, subcutaneous or intramuscular injection). Most preferably, the composition of this invention is administered orally or topically. When given orally, the composition of this invention is particularly suited to relieve symptom such as headaches, inflammation, hot flashes, mood disturbances and the like. When applied topically, the composition is particularly effective in relieving vaginal dryness and improving skin tone.

The orally administered embodiments of the herbal composition of this invention can be in any conventional form such as, e.g., capsules (hard or soft), tablets, elixirs, powders, granules, suspensions in water or non-aqueous media, sachets, as additives to food or beverages, or even can be made into a tea. Most preferably, the orally administered embodiment of the composition is in the form of a soft gel capsule which is swallowed with water.

For preparing solid orally administered compositions such as capsules or tablets, the principal active ingredients are mixed with a pharmaceutical carrier (e.g., conventional tableting ingredients such as corn starch, lactose, sucrose, sorbitol, talc, stearic acid, magnesium stearate, dicalcium phosphate or gums) and other pharmaceutical diluents (e.g., water) to form a solid preformulation composition containing a substantially homogenous mixture of the composition of this invention, or a non-toxic pharmaceutically acceptable salt thereof. When referring to the preformulation compositions as substantially homogenous, it is meant that the active ingredients are dispersed evenly throughout the composition so that the composition may be readily subdivided into equally effective unit dosage forms such as capsules, pins and tablets. This solid preformulation composition can then be subdivided into unit dosage forms containing, for example, from 0.15 to 1.0 gram, of the active-ingredient composition.

Liquid preparations for oral administration may take the form of, for example, solutions, syrups or suspensions, or they may be presented as a dry product for reconstitution with water or other suitable vehicles before use. Such liquid preparations may be prepared by conventional means with pharmaceutically acceptable additives such as suspending agents (e.g., sorbitol syrup, methyl cellulose, or hydrogenated edible fats); emulsifying agents (e.g., lecithin or acacia); non-aqueous vehicles (e.g., almond oil, oily esters or ethyl alcohol); preservatives (e.g., methyl or propyl p-hydroxybenzoates or sorbic acid); and artificial or natural colors and/or sweeteners.

The herbal composition of this invention can be combined with a physiologically acceptable oral vehicle into unit dosages. A unit dosage can comprise a therapeutically effective amount of each herbal extract for a single daily administration (e.g., orally), or it can be formulated into smaller quantities of each ingredient to provide for multiple doses in a day. A unit dosage will depend upon many factors including age, size, and condition of the woman being treated and the number of times the unit will be taken in a single day. In any event, the entire daily dosage will be that which is physiologically acceptable to an individual and can be administered daily over a prolonged period of time. In the present invention, normally between about 300 and 2000 mg of the active herb composition is preferably orally administered per day, with part of the total dose preferably taken at two or more different times during the day. When the orally administered composition is in the form of a capsule, the serving size of the composition is typically two capsules, with each capsule preferably containing from 0.15 to 1.0 gram of the active composition.

Formulations for topical administration may include but are not limited to lotions, ointments, gels, creams, suppositories, drops, liquids, sprays, and powders. Conventional pharmaceutical carriers; aqueous, powder or oily bases; thickeners and the like may be necessary or desirable. Most preferably, the topically administered embodiment of the composition of this invention is in the form of a cream.

Formulations for parenteral administration may include but are not limited to sterile aqueous solutions which may also contain buffers, diluents and other suitable additives. The active ingredients may be formulated for parenteral administration by injection, which includes using conventional catheterization techniques or infusion. Formulations for injection may be presented in unit dosage form, e.g., in ampules or in multi-dose containers, with an added preservative. The compositions may take such forms as suspensions, solutions or emulsions in oily or aqueous vehicles, and may contain formulating agents such as stabilizing, suspending or dispersing agents. Alternatively, the active ingredients may be in powder form for reconstitution with a suitable vehicle, e.g., sterile pyrogert-free water, before use.

The exact proportion of the extracts used in the composition of this invention will depend on the concentration of active ingredients found naturally in each component. Using the guidance provided herein and a basic knowledge of drug preparation and pharmacology, one skilled in the art could easily adjust the proportions of the separate components of the composition so as to obtain a composition which has the therapeutic effects discussed herein.

The present invention is also directed to methods of alleviating the symptoms associated with hormonal imbalance in women, involving orally, topically or administering an effective amount of the active-ingredient herbal composition of this invention to a woman. The term "effective amount" with respect to the active-ingredient herbal composition means that amount sufficient to alleviate the symptoms of hormonal imbalance. The effective amount will depend upon the severity of the symptoms and on the responsiveness of the patient to the herbal composition. Persons of ordinary skill in the art can easily determine optimum dosages, dosing methodologies, and repetition rates.

For topical use, the composition can be administered, e.g., ophtamically, vaginally, rectally, intranasally, and the like. If the topically administered embodiment of the composition of this invention is in the form of a skin cream, the composition is administered to the skin of the patient, including but not limited to the skin of the hands and face. If the composition is in the form of a vaginal ointment, the composition is administered to the vagina of the patient.

Suitable modes of parenteral administration include, e.g., intravenous drip; intraperitoneal, subcutaneous or intramuscular injection; and the like.

Oral administration is accomplished by ingesting the composition. As stated previously herein, the most preferred form of the orally administered composition of this invention is the soft gel capsule, which is preferably swallowed with water.

Presented in the table below is a particularly preferred embodiment of the orally administered soft gel capsule form of the composition of this invention. The formulation below is the combined compositions of two capsules. In other words, two capsules constitute a single serving or unit dose of the composition. Each capsule contains a portion of the overall composition.

TABLE

Orally Administered Herbal Composition:
Formulation Per Serving (Two Capsules)

| Ingredient | Amount (in milligrams) |
| --- | --- |
| Dong Quai (Angelica sinensis), root, extract (1% lingustilide - 0.80 mg) | 80 |
| Schizandra (wu-wei-zi), berry, extract (2% shizandrins - 1.6 mg) | 80 |
| Ginger, rhizome, certified organic, supercritical extract (minimum 20% pungent compounds - 10 mg, 5% zingiberene - 2.5 mg) | 50 |
| Black Cohosh, root & rhizome, extract (8% triterpene glycoside - 3.2 mg) | 40 |
| Chaste Tree, berry, extract (0.6% aucubin - 0.24 mg)(0.5% agnuside - 0.20 mg) | 40 |
| Rosemary, leaf & essential oil, supercritical extract (23% total phenolic antioxidants [TPA]- 2.3 mg) | 10 |

The composition set forth in the table above further contains evening primrose oil (seed) supercritical extract, olive oil (certified organic), and yellow beeswax.

The soft gel capsules containing the composition set forth in the table above are preferably composed of gelatin, vegetable glycerine, purified water and carob.

For oral administration of the above-recited formulation, two soft gel capsules (together constituting one serving) are preferably taken daily, with 8 ounces of water.

What is claimed is:

1. An orally administered herbal composition for promoting hormonal balance in women, comprising: about 80 milligrams of dong quai root extract; about 80 milligrams of schizandra berry extract; about 50 milligrams of certified organic ginger rhizome supercritical extract; about 40 milligrams of black cohosh root and rhizome extract. about 40 milligrams of chaste tree berry extract; and 10 milligrams of rosemary leaf and essential oil supercritical extract; wherein: the dong quai root extract comprises 1% by weight of lingustilide; the schizandra berry extract comprises about 2% by weight of shizandrins; the ginger supercritical extract comprises at least about 20% by weight of pungent compounds and about 5% by weight of zingiberene; the black cohosh extract comprises about 8% by weight of triterpene glycoside; the chaste tree berry extract contains about 0.6% by weight aucubin and about 0.5% by weight of agnuside; and the rosemary supercritical extract contains about 23% by weight of phenolic antioxidants.

2. A composition according to claim 1, wherein the orally administered composition is in a form selected from the group consisting of capsules, tablets, elixirs, powders, granules, suspensions, sachets, food additives, beverage additives, and tea.

3. A composition according to claim 2, wherein the orally administered composition is in the form of two soft gel capsules.

4. A method of alleviating symptoms associated with hormonal imbalance in a woman afflicted with such symptoms, comprising: orally administering to said woman an herbal composition comprising: about 80 milligrams of dong quai root extract; about 80 milligrams of schizandra berry extract; about 50 milligrams of certified organic ginger rhizome supercritical extract; about 40 milligrams of black cohosh root and rhizome extract; about 40 milligrams of chaste tree berry extract; and 10 milligrams of rosemary leaf and essential oil supercritical extract; wherein: the dong quai root extract comprises 1% by weight of lingustilide; the schizandra berry extract comprises about 2% by weight of shizandrins; the ginger supercritical extract comprises at least about 20% by weight of pungent compounds and about 5% by weight of zingiberene; the black cohosh extract comprises about 8% by weight of triterpene glycoside; the chaste tree berry extract contains about 0.6% by weight aucubin and about 0.5% by weight of agnuside; and the rosemary supercritical extract contains about 23% by weight of phenolic antioxidants.

5. A method according to claim 4, wherein the orally administered composition is in a form selected from the group consisting of capsules, tablets, elixirs, powders, granules, suspensions, sachets, food additives, beverage additives, and tea.

6. A method according to claim 4, wherein the orally administered composition is in the form of two soft gel capsules, further wherein the two soft gel capsules are administered to said woman on a daily basis.

* * * * *